US009040763B2

(12) United States Patent
Spieker et al.

(10) Patent No.: US 9,040,763 B2
(45) Date of Patent: May 26, 2015

(54) METHOD FOR QUENCHING PARAFFIN DEHYDROGENATION REACTION IN COUNTER-CURRENT REACTOR

(75) Inventors: Wolfgang A. Spieker, Glenview, IL (US); Laura E. Leonard, Western Springs, IL (US); David N. Myers, Hoffman Estates, IL (US)

(73) Assignee: UOP LLC, Des Plaines, IL (US)

( * ) Notice: Subject to any disclaimer, the term of this patent is extended or adjusted under 35 U.S.C. 154(b) by 839 days.

(21) Appl. No.: 12/824,640

(22) Filed: Jun. 28, 2010

(65) Prior Publication Data

US 2011/0319692 A1  Dec. 29, 2011

(51) Int. Cl.
C07C 5/333 (2006.01)

(52) U.S. Cl.
CPC .............. *C07C 5/333* (2013.01); *Y10S 585/903* (2013.01); *Y10S 585/91* (2013.01); *Y10S 585/911* (2013.01)

(58) Field of Classification Search
USPC .................. 585/654, 655, 659, 910, 903, 911
See application file for complete search history.

(56) References Cited

U.S. PATENT DOCUMENTS

| | | | |
|---|---|---|---|
| 2,458,862 A * | 1/1949 | Krebs ............................ | 585/628 |
| 3,288,878 A * | 11/1966 | Hachmuth ..................... | 585/659 |
| 3,978,150 A | 8/1976 | McWilliams, Jr. | |
| 4,663,493 A * | 5/1987 | Vora et al. ..................... | 585/655 |
| 5,026,935 A | 6/1991 | Leyshon et al. | |
| 5,026,936 A | 6/1991 | Leyshon et al. | |
| 5,043,522 A | 8/1991 | Leyshon et al. | |

FOREIGN PATENT DOCUMENTS

| | | |
|---|---|---|
| EP | 109060 B1 | 3/1987 |
| EP | 109059 B1 | 7/1987 |

OTHER PUBLICATIONS

Shilling, et al., "Heat Transfer Equipment" in Perry's Chemical Engineer's Handbook, McGraw-Hill, 7th ed., 1997, available on-line at www.knovel.com.*
Tilton, "Fluid and Particle Dynamics" in Perry's Chemical Engineer's Handbook, 7th ed., 1997, McGraw-Hill, available on-line at www.knovel.com.*
Kaiser, V., et al.; Better Ethylene Separation Unit, Hydrocarbon Processing, Nov. 1988, pp. 57-61.

* cited by examiner

*Primary Examiner* — In Suk Bullock
*Assistant Examiner* — Bradley Etherton
(74) *Attorney, Agent, or Firm* — Arthur E Gooding

(57) ABSTRACT

A process is presented for quenching a process stream in a paraffin dehydrogenation process. The process comprises cooling a propane dehydrogenation stream during the hot residence time after the process stream leaves the catalytic bed reactor section. The process includes cooling and compressing the product stream, taking a portion of the product stream and passing the portion of the product stream to the mix with the process stream as it leaves the catalytic bed reactor section.

18 Claims, 1 Drawing Sheet

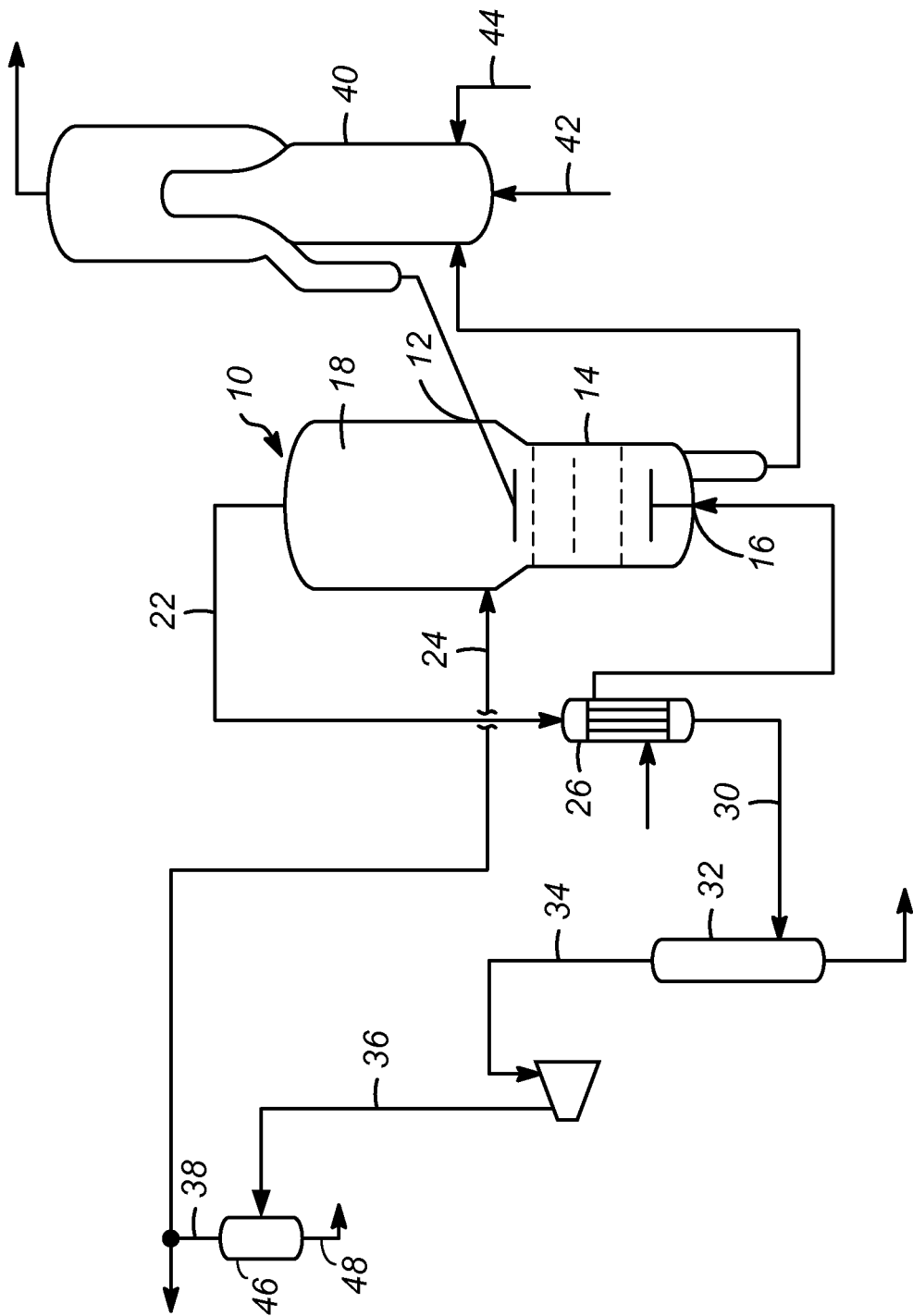

METHOD FOR QUENCHING PARAFFIN DEHYDROGENATION REACTION IN COUNTER-CURRENT REACTOR

FIELD OF THE INVENTION

The present invention involves processes for the dehydrogenation of paraffins. The processes generate a hot product stream and the invention is related to the cooling of the hot product stream.

BACKGROUND OF THE INVENTION

The production of light olefins, and in particular ethylene and propylene, are important for the production of numerous plastics, and for the production of commercially important monomers. The plastics include polyethylene and polypropylene, and monomers include vinyl chloride, ethylbenzene, ethylene oxide, and some alcohols. Light olefins are traditionally produced through cracking, both steam and catalytic cracking, of hydrocarbon feedstocks comprising larger hydrocarbons. Feedstocks include naphthas, and other heavier hydrocarbon streams.

The traditional method of olefin production is the cracking of petroleum feedstocks to olefins. The cracking of petroleum feedstocks is done through catalytic cracking, steam cracking, or some combination of the two processes. The olefins produced are generally light olefins, such as ethylene and propylene. There is a large market for the light olefin products of ethylene and propylene. As petroleum feedstocks from crude oil face increasing prices it is advantageous to provide for other sources of ethylene and propylene. It is also known that olefins can be produced from oxygenates. The most common conversion of oxygenates to olefins is the production of light olefins from methanol, wherein methanol can be produced from other sources, including biomass, and natural gas.

An ethylene plant is a very complex combination of reaction and gas recovery systems. The feedstock is charged to a cracking zone in the presence of steam at effective thermal conditions to produce a pyrolysis reactor effluent gas mixture. The pyrolysis reactor effluent gas mixture is stabilized and separated into purified components through a sequence of cryogenic and conventional fractionation steps. A typical ethylene separation section of an ethylene plant containing both cryogenic and conventional fractionation steps to recover an ethylene product with a purity exceeding 99.5% ethylene is described in an article by V. Kaiser and M. Picciotti, entitled, "Better Ethylene Separation Unit." The article appeared in HYDROCARBON PROCESSING MAGAZINE, November 1988, pages 57-61 and is hereby incorporated by reference.

Methods are known for increasing the conversion of portions of the products of the ethylene production from a zeolitic cracking process to produce more propylene by a disproportionation or metathesis of olefins. Such processes are disclosed in U.S. Pat. No. 5,026,935 and U.S. Pat. No. 5,026,936 wherein a metathesis reaction step is employed in combination with a catalytic cracking step to produce more propylene by the metathesis of $C_2$ and $C_4$ olefins obtained from cracking The catalytic cracking step employs a zeolitic catalyst to convert a hydrocarbon stream having 4 or more carbon atoms per molecule to produce olefins having fewer carbon atoms per molecule. The hydrocarbon feedstream to the zeolitic catalyst typically contains a mixture of 40 to 100 wt-% paraffins having 4 or more carbon atoms per molecule and 0 to 60 wt-% olefins having 4 or more carbon atoms per molecule. In U.S. Pat. No. 5,043,522, it is disclosed that the preferred catalyst for such a zeolitic cracking process is an acid zeolite, examples includes several of the ZSM-type zeolites or the borosilicates. Of the ZSM-type zeolites, ZSM-5 was preferred. It was disclosed that other zeolites containing materials which could be used in the cracking process to produce ethylene and propylene included zeolite A, zeolite X, zeolite Y, zeolite ZK-5, zeolite ZK-4, synthetic mordenite, dealuminized mordenite, as well as naturally occurring zeolites including chabazite, faujasite, mordenite, and the like. Zeolites which were ion-exchanged to replace alkali metal present in the zeolite were preferred. Preferred alkali exchange cations were hydrogen, ammonium, rare earth metals and mixtures thereof.

European Patent No. 109,059B1 discloses a process for the conversion of a feedstream containing olefins having 4 to 12 carbon atoms per molecule into propylene by contacting the feedstream with a ZSM-5 or a ZSM-11 zeolite having a silica to alumina atomic ratio less than or equal to 300 at a temperature from 400 to 600° C. The ZSM-5 or ZSM-11 zeolite is exchanged with a hydrogen or an ammonium cation. The reference also discloses that, although the conversion to propylene is enhanced by the recycle of any olefins with less than 4 carbon atoms per molecule, paraffins which do not react tend to build up in the recycle stream. The reference provides an additional oligomerization step wherein the olefins having 4 carbon atoms are oligomerized to facilitate the removal of paraffins such as butane and particularly isobutane which are difficult to separate from $C_4$ olefins by conventional fractionation. In a related European Patent No. 109,060B1, a process is disclosed for the conversion of butenes to propylene. The process comprises contacting butenes with a zeolitic compound selected from the group consisting of silicalites, boralites, chromosilicates and those zeolites ZSM-5 and ZSM-11 in which the mole ratio of silica to alumina is greater than or equal to 350. The conversion is carried out at a temperature from 500° C. to 600° C. and at a space velocity of from 5 to 200 kg/hr of butenes per kg of pure zeolitic compound. The European Patent No. 109,060B1 discloses the use of silicalite-1 in an ion-exchanged, impregnated, or co-precipitated form with a modifying element selected from the group consisting of chromium, magnesium, calcium, strontium and barium.

Paraffin dehydrogenation represents an alternative route to light olefins and is described in U.S. Pat. No. 3,978,150 and elsewhere. This is an important process as it provides control through the selection of the feedstream. One can selectively dehydrogenate a feedstream comprised primarily of the paraffin of choice, such as the conversion of propane to propylene. However, problems exist in the conversion of paraffins, and in undesired side reactions that affect the yields, and therefore affect the economics of producing light olefins through paraffin dehydrogenation.

SUMMARY OF THE INVENTION

The invention provides a new process for controlling the temperatures of an exiting process stream from a dehydrogenation reactor. The process includes passing a hot catalyst to the dehydrogenation reactor wherein the catalyst flows down through the reactor. A paraffin rich stream is passed to the dehydrogenation reactor wherein the paraffin stream flows up through the reactor, contacting the catalyst and generating a process stream. The process stream comprises olefins and carries some catalyst fines from the reaction section of the reactor. The catalyst and catalyst fines are separated from the process stream to generate a product stream. The product stream is cooled and compressed to create a cooled product stream. A portion of the cooled product stream is passed to the dehydrogenation reactor to quench the process stream. The cooled product stream portion is passed to a position proximate to the top of the catalytic reaction section of the reactor.

The invention provides for cooling of the process stream to prevent undesired side reactions, while not incurring additional separation costs, or complexity to a dehydrogenation process. This is of particular use in the production of light olefins, and in particular the conversion of propane to propylene.

Additional objects, embodiments and details of this invention can be obtained from the following drawing and detailed description of the invention.

BRIEF DESCRIPTION OF THE DRAWING

The FIGURE is a process flow diagram of the dehydrogenation process of the present invention.

DETAILED DESCRIPTION OF THE INVENTION

The production of propylene is important for the production of polypropylene. An important aspect is the selectivity in the economics of the production process. The process involves high temperature reactions, and can lead to undesired side reactions that decreases the propylene production. One aspect is the hot residence time of the process stream before the product stream leaves the reactor. The hot residence time during separation of the catalyst from the process stream leads to non-selective cracking. Minimizing hot residence time improves product quality, which can be performed by quenching of the hot process stream. Normal quenching processes involve the injection of steam or an inert gas, or even hydrogen. However, each of these quenching materials present problems, and can increase costs through additional separation sections. The present invention provides for cooling, or quenching, of the process stream and decreases, or prevents, unwanted cracking, thereby improving propylene yields.

The present invention is illustrated in the FIGURE showing the process flow for controlling the temperature of the product coming from the dehydrogenation reactor. The process comprises passing catalyst to a dehydrogenation reactor 10 through a catalyst inlet port 12. The catalyst is cycled through the reactor and a regenerator. The reactor can be a bubbling bed reactor, or other type of reactor where the catalyst flows through the reactor and has an average residence time before being recycled to a regenerator. In one embodiment, the catalyst is distributed over a series of trays with openings to allow the catalyst to flow down through the reactor section 14. A paraffin rich stream is passed to the dehydrogenation reactor 10 through a feedstream inlet port 16. The reactor section 14 generates a process stream comprising dehydrogenated hydrocarbons, some unconverted paraffins and some catalyst that is entrained in the process stream. The catalyst is separated from the process stream in a separation section 18, thereby creating a product stream 22, comprising dehydrogenated hydrocarbons. The product stream 22 is cooled and a portion of the cooled product stream 24 is passed back to the reactor 10 to mix with the process stream.

Preferably, the cooled product stream 24 is passed to a position in the reactor 10 just above the catalyst, or proximate to the top of the reactor section 14 of the reactor 10. Catalyst entering the reactor 10 is preferably passed through a distributor for depositing catalyst in a substantially uniform manner over the top of the reactor section 14. The cooled product stream 24 is preferably passed to a position above the catalyst distributor.

In one embodiment, the product stream 22 is passed through a combined feed heat exchanger 26, wherein the product stream 22 is cooled, and a combined feed of hydrogen and paraffins are preheated before passing the paraffin rich feedstream to the dehydrogenation reactor 10. The cooled product stream 30 can be further cooled through a contact heat exchanger 32 to further cool the product stream and to recover any catalyst fines. In one embodiment, the contact heat exchanger 32 is a direct liquid contact cooler. The cooled product stream 34 is compressed to generate a compressed product stream 36. The compressed product stream 36 is further cooled in a cooling vessel 46 to remove the heat of compression, and a compressed cooled product stream 38 is generated. Condensate 48 generated in the cooling vessel 46 is passed out of the cooling vessel 46. A portion 24 of the compressed cooled product stream 38 is then passed to the dehydrogenation reactor 10.

One method of controlling the amount of cooling can be assisted through the setting of the compression level of the product stream. The product stream can be compressed to a level above the reactor pressure, and the expansion of the compressed and cooled product stream when entering the reactor can provide some additional cooling. The amount of product stream passed to quench the process stream is determined by the cooling load necessary to reduce the process stream temperature to below typical cracking temperatures.

The reactor is sized to process a feedstream having a superficial velocity between 0.1 and 1.4 msec. The reactor separation section 18 is also sized to maintain a superficial velocity of the process stream and the returned cooled product stream to a value between 0.1 and 1.4 msec. To that extent, the separation section has an enlarged diameter, relative to the reaction section diameter, to maintain the superficial velocity within the design range. In a preferred process, the superficial velocity is more tightly controlled to be in the range of 0.2 and 1 msec, and a more preferred range of 0.3 and 0.8 msec, and most preferably the superficial velocity is approximately 0.6 msec.

By the term "superficial velocity", it is meant the velocity of the gas as it flows through the vessel. The superficial velocity is typically determined by dividing the volumetric flow rate of the gas by the cross-sectional area of the vessel. The vessel design is such that the separation zone has a diameter that is greater than the diameter of the reaction vessel in the region of the catalyst beds. The initial expansion allows for significant settling out of the catalyst from the process stream. The vessel diameter is increased to accommodate the increased gas flow from the recycled cooled product stream to maintain a superficial velocity in the desired range.

Catalyst flows through the reactor section 14 of the reactor 10, and is passed to a regeneration unit 40. The catalyst is regenerated through combustion of the carbon that accumulates on the catalyst during the dehydrogenation process. The carbon is combusted to heat up the catalyst with compressed air 42 in the regenerator 40. Additional fuel 44 can be added to the regenerator 40 to control the combustion. Regenerated catalyst is then passed out of the regenerator 40 to the dehydrogenation reactor 10.

Catalyst can be passed to any reactor design that allows for the catalyst to flow through the reactor, with the catalyst recovered and passed to the regenerator. One such design is a fluidized bed with catalyst added to the top of the reactor section, and catalyst withdrawn from the bottom of the reactor section. Another design is the use of reactor internals for spreading the catalyst across the reactor and allowing the catalyst to then flow downward from one reactor internal section to another reactor internal section. An example of appropriate reactor internals is the use of trays, or grids, having small openings, either slits or holes, for the vapor to flow upward, and large openings to allow for catalyst to flow downward. The larger openings are spaced to have the catalyst flow all, or partway, across the tray, or grid, with lower trays having the larger openings positioned in a transverse position relative to a position of the large openings in the tray above. The trays can also include sections that have no holes to insure the distribution of vapor flowing through the trays. The use of trays for flowing the catalyst through the reactor is preferred over a series of bubbling bed reactors as bubbling bed reactors require a space over each bed to separate most of the catalyst. The space above the bubbling beds provides an undesired dilute phase residence time, that is a low catalyst to hydrocarbon ratio phase. This space has the drawback of contributing to hot dilute phase residence time and contributes to reducing the selectivity. The present design reduces the hot dilute phase residence time by quenching the process stream during the separation of catalyst from the process stream.

In one embodiment, the dehydrogenation reactor can include a plurality of catalyst feeds to the reactor section 14. In this embodiment, a catalyst inlet port directs catalyst above each tray of catalyst and distributes catalyst over each tray. The catalyst then flows down through the reactor section 14.

The dehydrogenation reactor 10 comprises a reactor section 14 that allows for the flow of catalyst down through the reactor section 14. This includes different reactor designs, such as a fluidized bed. The preferred reactor section design 14, comprises perforated trays having large openings, wherein the perforations allow for the process vapor stream to flow upward through the reactor. The large openings allow for the flow of catalyst to pour from one tray to a lower tray. In one design, the trays appear as sections having large openings across the length of the trays, with the trays positioned to have the perforated sections of the trays overlapping the large openings such that the catalyst will flow in a transverse direction across each tray before flowing to the next tray below.

In one embodiment, the process comprises passing catalyst to a dehydrogenation reactor through at least one catalyst inlet port. The catalyst inlet port is in fluid communication with a catalyst distribution manifold for distributing catalyst over the top of a catalyst tray. A feedstream comprising propane is passed to the dehydrogenation reactor through a distributor at the bottom of the reactor. The feedstream passes through the reactor section and creates a process stream comprising light olefins, and catalyst. The light olefins in the process stream are predominantly propylene. Catalyst is separated from the process stream to create a product stream, and the catalyst is returned to the reactor section. The product stream is passed to a cooling unit, thereby creating a cooled product stream. The cooled product stream is passed to mix with the process stream at a position above the catalyst distribution manifold, thereby quenching the process stream and limiting further thermal reactions in the process stream, such as thermal cracking.

The preferred embodiment is a dehydrogenation reactor comprising trays for spreading the catalyst and flowing the catalyst across the trays and down through the reactor. In an alternate configuration, the catalyst is passed to the dehydrogenation reactor through a plurality of catalyst inlet ports. Each inlet port is connected to a catalyst distribution manifold, and each catalyst distribution manifold deposits the catalyst over a different tray. In the embodiment with multiple catalyst inlet ports, the cooled product stream is passed to a position above the uppermost catalyst distribution manifold.

In a preferred embodiment, the cooled product stream is passed proximate to the uppermost catalyst distribution manifold in a position above the manifold. This cooled product inlet position is near the lower portion of the upper separation section of the dehydrogenation reactor.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for controlling temperatures in a dehydrogenation reactor, comprising:
    passing a catalyst to a dehydrogenation reactor, such that the catalyst flows down through the reactor;
    passing a paraffin rich stream to the dehydrogenation reactor such that the paraffin rich stream flows up through the reactor and through a catalyst bed, thereby creating a process stream comprising catalyst and dehydrogenated hydrocarbons and some unconverted paraffins;
    separating the vapor phase from the process stream thereby creating a product stream;
    passing the product stream to a cooling unit, thereby creating a cooled product stream;
    compressing the cooled product stream, thereby creating a compressed cooled product stream;
    cooling the compressed cooled product stream thereby creating a cooled compressed cooled product stream; and
    passing a portion of the cooled compressed cooled product stream to mix with the process stream in the reactor above the catalyst bed, wherein the cooled compressed cooled product stream expands upon entry to the reactor, and wherein the temperature of the process stream is reduced below the cracking temperature of the dehydrogenated paraffins.

2. The process of claim 1 wherein the cooled product stream is passed to the process stream above where the catalyst enters the dehydrogenation reactor.

3. The process of claim 1 wherein the cooling unit comprises passing the product stream through a contact cooler.

4. The process of claim 1 wherein the superficial velocity of the process stream is between 0.1 and 1.4 msec.

5. The process of claim 4 wherein the superficial velocity of the process stream is between 0.2 and 1 msec.

6. The process of claim 1 wherein the cooled product stream is passed to the process stream at a position proximate to the top of the uppermost catalyst bed.

7. The process of claim 1 wherein the cooling unit is a combined feed heat exchanger.

8. A process for controlling temperatures in a dehydrogenation reactor, comprising:
    passing a catalyst to a dehydrogenation reactor through at least one catalyst inlet port;
    passing a propane rich stream to the dehydrogenation reactor through a distributor at the bottom of the reactor, thereby creating a process stream comprising catalyst and dehydrogenated hydrocarbons;
    separating the catalyst from the process stream thereby creating a product stream, comprising light olefins;
    cooling the product stream in a cooling unit, thereby creating a cooled product stream;
    compressing the cooled product stream, thereby creating a compressed cooled product stream;

cooling the compressed cooled product stream thereby creating a cooled compressed cooled product stream; and passing a portion of the cooled compressed cooled product stream to mix with the process stream to a position above the catalyst inlet port, wherein the cooled compressed cooled product stream expands upon entry to the reactor, and wherein the temperature of the process stream is reduced below the cracking temperature of the dehydrogenated hydrocarbons.

9. The process of claim 8 wherein the dehydrogenation reactor comprises reactor internals for spreading the catalyst and flowing the catalyst across the reactor internals and down through the reactor.

10. The process of claim 8 wherein the catalyst flows down through the reactor.

11. The process of claim 8 wherein the catalyst is passed to the dehydrogenation reactor through at least one catalyst inlet port, and wherein each inlet port admits catalyst to a separate reactor internal.

12. The process of claim 8 wherein the dehydrogenation reactor comprises a lower section for contacting the propane rich stream with the catalyst and an upper section for separation of the process stream from the catalyst.

13. The process of claim 12 wherein the cooled product stream is passed proximate to the lower portion the upper section.

14. The process of claim 12 wherein the cooled product stream is passed to the upper portion of the reactor to maintain a superficial velocity between 0.1 m/s to 1.4 m/s.

15. The process of claim 14 wherein the cooled product stream is passed to the upper portion of the reactor to maintain a superficial velocity between 0.2 m/s to 1 m/s.

16. A process for controlling temperatures in a dehydrogenation reactor, comprising:

passing a catalyst to a dehydrogenation reactor through at least one catalyst inlet port, wherein the dehydrogenation reactor has a lower reactor section for contacting catalyst with a feedstream and an upper section for separation of catalyst from a process stream;

passing a paraffin rich stream to the dehydrogenation reactor through an inlet distribution system at the bottom of the reactor;

contacting the catalyst and the paraffin rich stream in a counter-current flow system with the catalyst flowing downward through the reactor and the paraffin rich stream flowing upward through the reactor, thereby creating a process stream separating the catalyst from the process stream thereby creating a product stream, comprising olefins;

passing the product stream to a cooling unit, thereby creating a cooled product stream;

compressing the cooled product stream, thereby creating a compressed cooled product stream;

cooling the compressed cooled product stream thereby creating a cooled compressed cooled product stream; and passing a portion of the cooled compressed cooled product stream to mix with the process stream, wherein the cooled compressed cooled product stream expands upon entry to the reactor, and wherein the temperature of the process stream is reduced below the cracking temperature of the dehydrogenated paraffins.

17. The process of claim 16 wherein the cooled product stream is passed to the bottom of the upper section of the reactor.

18. The process of claim 16 wherein the cooled product stream is passed to the upper section of the reactor at a rate to maintain a superficial velocity of the process stream mixed with the cooled product stream at a velocity between 0.2 m/s to 1 m/s.

* * * * *